United States Patent [19]

Reischig et al.

[11] Patent Number: 4,812,481

[45] Date of Patent: Mar. 14, 1989

[54] SYNERGISTIC COMBINATION OF AMANTADIENE AND SELEGILINE

[75] Inventors: Dirk Reischig, Bad Homburg; Helmut Hettche, Offenbach; Wolfgang Brade, Wehrheim, all of Fed. Rep. of Germany

[73] Assignee: Degussa Aktiengesellschaft, Frankfurt am Main, Fed. Rep. of Germany

[21] Appl. No.: 38,566

[22] Filed: Apr. 15, 1987

[30] Foreign Application Priority Data

Apr. 16, 1986 [DE] Fed. Rep. of Germany ....... 3612702

[51] Int. Cl.⁴ .................... A61U 31/13; A61U 31/135
[52] U.S. Cl. ...................................... 514/647; 514/661
[58] Field of Search ............................... 514/647, 661

[56] References Cited

FOREIGN PATENT DOCUMENTS 0146363 12/1984 European Pat. Off. .
2253130 7/1973 Fed. Rep. of Germany .
314077 3/1974 Fed. Rep. of Germany .

OTHER PUBLICATIONS

Austria-Codex Fachinformation 1985/86.
Die Pharmazie 37 (1982).
Index Nominum 1975/76 (Zurich, Switz.).
Drug Development Research 7:125-140 (1986).
Chemical Abstracts vol. 101, 1985, p. 64.
Chemical Abstracts, vol. 102, 1985, p. 64.
Felice, J. Neurochemistry, vol. 31, pp. 1461-1465 (1978) (Great Britain).
Sperk, J. Neurochemistry, vol. 38, pp. 840-843 (1982) (New York).
Webster, Med. Treat., vol. 5, pp. 257-282 (1968) (New York).
Department of Catecholamines in Rat Brain Parts by Reverse-Phase Ion-pair Liquid Chromatography, Felice et al., Journal of Neurochemistry.
Simultaneous Determination of Serotonin, 5-Hydroxyindoleacetic Acid . . . Guther Sperk, Journal of Neurochemistry.
Critical Analysis of the Disability in Parkinson's Disease Neurology Service, Veterans Administration Med. Treat. (N.Y.) 5 257-282 (1968).

Primary Examiner—Stanley J. Friedman
Attorney, Agent, or Firm—Cushman, Darby & Cushman

[57] ABSTRACT

There are provided in medicaments with synergistic action containing a combination of amantadine and selegiline.

5 Claims, No Drawings

SYNERGISTIC COMBINATION OF AMANTADIENE AND SELEGILINE

BACKGROUND OF THE INVENTION

Amantadine is a virustatic agent as well as an anti-Parkinsonism drug. The chemical designation is 1-amino-adamantane.

Selegiline is an anti-depressant as well as an appetite depressant. The chemical designation is N-(1-phenyl-2-propyl)-N-methyl-2-propinylamine.

SUMMARY OF THE INVENTION

It has been discovered that the action of amantadine and its salts is surprisingly increased synergistically by combination with selegiline or salts of selegiline.

The invention has the task of preparing an improved medicament for the treatment of Parkinson's disease.

The invention is directed to the combination of the active substances amantadine and selegiline, whereby these active substances can also be present in the form of their salts with physiologically harmless acids. The weight amounts and weight parts indicated in the specification and in the claims refer to the pure active substances, that is, not to salts of these active substances.

Amantadine and selegiline are preferably used as acid addition salts, whereby the salts with hydrohalic acids (e.g. the hydrochloride) or with organic acids (e.g. the citrate) are particularly interesting.

The combination of the invention displays, e.g. in the case of Parkinson's disease, a surprising synergistic action which is synergistically increased compared to the action of pure amantadine. Selegiline alone, in contrast, exhibits almost no anti-Parkinsonism action.

The following, for example, can be an experimental model for an anti-Parkinsonism action: Animal experiments:

The substances which come in question as anti-Parkinsonism drugs are tested using the elevation of the concentration of dopamine or the conversion of dopamine (e.g. dopamine to DOPAC=3,4-dihydroxxyphenyl acetic acid or dopamine to homovanillic acid=3-methoxy-4-hydroxyphenyl acetic acid) in the corpus striatum (brain area in the extrapyramidal motor system; designation for a part of the basal stem ganglia) of Mongolian jumping mice. The prepared corpus striatum specimens are analyzed for dopamine by means of high pressure liquid chromatography (HPLC-ESA-ECD; of, Felice et al., J. Neurochemistry 31, 1973, p. 1461) and for homovanillic acid and DOPAC by means of high pressur liquid chromatography (HPLC-BAS-ECD; of Sperk, J. Neurochemistry 38, 1982, p. 840). Experimental animals of both sexes with a weight of 70 to 80 g are selected thereby.

The substances are injected intraperitoneally (into the abdominal cavity) in concentrations of 8.8–200 mg selegiline hydrochloride per ml and 3–40 mg amantadine hydrochloride per ml. Groups of 5 mice each receive amantadine doses of 0.5–400 mg/kg, e.g 1–100 mg/kg each and selegiline doses of 0.04–200 mg/kg, e.g. 0.1–50 mg/kg each for determining the ED 50 values.

For the determination of the synergistic effect, different fractions and multiples (e.g. from 0.01 times to 2 times) of the selegiline-ED 50 dose are combined. The animals are killed at different times (e.g. after 0.5–6 hours) after application of the individual substances or of the combination of the individual substances and the corpus striatum specimens are removed.

The homogenized specimens are tested for their content of dopamine, DOPAC and homovanillic acid by HPLC.

A synergistic effect can be shown if the values for dopamine, DOPAC and homovanillic acid are elevated in relation to the values at the administration of the individual substances. Examination methodology in human:

The effect of the anti-Parkinsonism action is established, for example, by Webster, D. D., Med. Treat. (N.Y.) 5, pp. 257–282, 1968. Here, the different symptoms are assigned and weighted after application of the monosubstance amantadine or the combination:

1. Slowed motor response of the hands
2. Rigor (elevation of the muscle tone)
3. Bent-over posture
4. Simultaneous swinging of the upper extremities
5. Walk
6. Tremor (trembling)
7. Facial expression
8. Seborrhea
9. Speech
10. Ability to stand alone.

An anti-Parkinsonism action is present if the sum of the values resulting from the Webster scale (the so-called disability score) is lower than the initial value without medication ($<30$). The synergistic effect of the combination results from the following: When selegiline is used in addition, the sum of the disability score is lower than that which would have been achieved if only amantadine had been used and/or the duration of the the effectiveness of amantadine is extended.

The synergistic effect in using the combination of the invention in the early states of Morbus Parkinsonism:

The earliest possible dispensation of the monoaminooxidase-$\beta$-inhibitor selegiline is valuable because of the progressive inhibiting effect of the illness. Since selegiline alone does not show sufficient effect in regard to improving the symptoms of the Parkinson symptomatics, it is unexpected that after the simultaneous giving of amantadine the relatively weak effect of the selegiline is increased synergistically (lowering of the Webster-sums-courses). Accordingly the patients for the first time are offered a possible therapy in the early phase of his illness, delays the advance of the Morbus Parkinson, improves the total symptoms satisfactorily and simultaneously holds astonishingly low the rate of side effects.

Synergistic effect of the combination of the invention with critical deteriorations of the Morbus Parkinson: The relatively slowly setting in improvement of the akinetic crisis after intravenous supply of amantadiene surprisingly can be accelerated by the addition of selegiline. The accordingly observed effect is decided and maintained longer than after the single addition of the individual components.

The synergistic elevation of action in humans is especially distinct if at least 20 mg amantadine and at least 1 mg selegiline are present in the combination.

The combinations of the invention can be considered, for example, for the following indications: Morbus Parkinson in all stages of the disease, depressions, naroolepsy, cerebro-organic psychosyndrome.

The daily doses of the combination of the invention are, e.g., 20 to 4000 mg, preferably 50 to 3000 mg and especially 100 to 2000 mg amantadine and 1 to 250 mg, preferably 3 to 300 mg, especially 4 to 150 mg selegiline.

The daily dose can be used in the form of a single administration of the entire amount or in the form of 1 to 5, especially 1 to 4 partial doses per diem. In general, an administration 1 to 3 times, especially 1 to 2 times daily is preferred. For example, the preferred dose for the combination of amantadine and selegiline is preferably 100 to 400 mg amantadine and 4 to 30 mg selegiline 1 to 3 times daily. This dose is especially approximately 250 mg amantadine and approximately 10 mg selegiline 1 to 3 times daily.

Amantadine and selegiline are present in a dosing unit e.g. in the following weight ratio: 1 part by weight selegiline is combined for example with 0.4–800 parts by weight amantadine, preferably 1 part by weight selegiline with 1.2–200 parts by weight amantadine, especially 1 part by weight selegiline with 3.3–100 parts by weight amantadine.

For example, the combinations 20–800 mg amantadine and 1–50 mg selegiline, preferably 50–600 mg amantadine and 3–40 mg selegiline, especially 100–400 mg amantadine and 4–30 mg selegiline, particularly 200–300 mg amantadine and 5–15 mg selegiline can be easily formulated to medicament.

The weight amounts indicated above are valid only for homogeneous mixtures of amantadine and selegiline (e.g. suppositories or single-layer tablets). In the case of other formulations, e.g. capsules and two-layer tablets, the components can of course also be combined in other weight amounts.

The dosage unit of the combination of the invention can contain, for example:

(a) In peroral medicaments:
20–800 mg amantadine, preferably 50–600 mg, especially 100–400 mg amantadine and 1–50 mg, preferably 3–40 mg, especially 4–30 mg selegiline.

These doses can be administered, for example, 1 to 5 times, preferably 1 to 4 times, especially 1 to 3 times daily.

(b) In parenteral medicaments (e.g. intravenous, intramuscular):
20–800 mg amantadine, preferably 50–600 mg, especially 100–400 mg amantadine and 1–50 mg, preferably 3–40 mg, especially 4–30 mg selegiline.

These doses can be administered, for example, 1 to 5, preferably 1 to 4, especially 1 to 3 times daily.

(c) In medicaments for rectal or vaginal application:
20–800 mg amantadine, preferably 50–600 mg, especially 100–400 mg amantadine and 1–50 mg, preferably 3–40 mg, especially 4–30 mg selegiline.

These doses can be administered, for example, 1 to 5, preferably 1 to 4, especially 1 to 3 times daily.

(d) In medicaments for application to the skin and mucous membranes (e.g. as solutions, lotions, emulsions, salves, plasters, etc.):
20–800 mg amantadine, preferably 50–600 mg, especially 100–400 mg amantadine and 1–50 mg, preferably 3–40 mg, especially 4–30 mg selegiline.

These doses can be administered, for example, 1 to 5, preferably 1 to 4, especially 1 to 3 times daily.

Of course, galenic preparations can also be produced which contain 2 to e.g. 6 times the dosage units indicated above.

The doses and weight parts indicated in the preceding pages which relate to human application refer to the free bases.

The acute toxicity of the combination of the invention in the mouse (expressed by the LD 50 mg/kg; method: Lithfield and Wilcoxon, J. Pharmacol. Exper. Ther. 95: p. 99, 1959) is, for example, for the combination amantadine (HCl salt) and selegiline (HCl salt) (weight ratio 10:1) between 600–700 mg/kg in oral application.

The combination of the invention is suitable for producing pharmaceutical compounds and preparations. The pharmaceutical compounds or medicaments contain the combination of the invention as active substance in one formulation. However, the individual active substances of the combination can also be present in separate formulations, whereby the amounts of active substance already indicated as used for the dosage unit in question. The active substances or active substance combination are optionally present in a mixture with other pharmacologically or pharmaceutically active substances.

The medicaments are produced in a known manner, whereby the known and customary pharmaceutical adjuvants as well as other customary carrier and diluting agent can be used.

As carriers and assistants, for example, are those recommended or given in the following literature as adjuvants for pharmacy, cosmetic, and related fields such as in Ullmann's Encyklopadie der technischen Chemie, Vol. 4 (1953), pages 1–39; Journal of Pharmaceutical Sciences 52 (1963), pages 819 et seq.; H. v. Czetsch-Lin-Gebiete; Phar. Ind. 2 (1961), pages 72 et seq.; Dr. H. P. Fiedler, Lexicon angrezende Gebiete, Cantor Kg. Aulendorf in Wurttemberg (1981).

Examples of such materials include gelatins, natural sugars such as sucrose or lactose, lecithin, pectin, starch (for example cornstarch), alginic acid, tylose, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, mehtyl cellulose, ??? cellulose, ??? cellulose phthalate, stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane).

Other adjuvants can also be substances which bring about decomposition (so-called explosives) such as: cross-linked polyvinyl pyrrolidone, sodium carboxy methyl starch, sodium carboxy methyl cellulose or microcrystalline cellulose. Likewise, known coating agents such as e.g. polyacrylates, cellulose ethers and the like can be used.

For the production of solutions, there can be used water of physiologically compatible organic solvents, as for example, ethanol, 1,2-propylene glycol, polyglycols, e.g., diethylene glycol, triethylene glycol and dipropylene glycol and their derivatives dimethyl sulfoxide, fatty alcohols, e.g., stearyl alcohol, cetyl alcohol, lauryl alcohol and oleyl alcohol, triglycerides, e.g. glyceryl olelate glyceryl stearate, glyceryl palmitate, and glyceryl acetate, partial esters of glycerine, e.g., glyceryl monostearate, glyceryl distearate, glyceryl monopalmitate, paraffins, and the like.

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, polyethylene oxide condensation products of fatty alcohols, alkyl phenolene or fatty acids or also 1-methyl-3-(2-hydroxyethyl)imidazolidone-(2). The term polyoxyethylated means in this context that the substances in question contain polyoxyethylene chains whose degree ° polymerization is generally between 2 to 40 and especially between 10 to 20.

Such polyoxyethylated substances can be obtained, for example, by reacting compounds containing hydroxyl groups (e.g. mono or diglycerides or unsaturated compounds such as, e.g., those containing the oleic acid residues) with ethylene oxide (e.g. 40 moles ethylene oxide per mole glyceride). Examples of oleotriglycerides are olive oil, peanut oil, castor oil, seasame oil, cotton seed oil and corn oil. See also Dr. H. P. Fiedler, "Lexicon derHilfastoffe fu Pharmazie, Kosmetik and angrezende Gebiete" [Lexicon of Adjuvants for Pharmacy, Cosmetics an Related Areas], 1971, pp. 191-195.

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodiummeta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

The pharmacological and galenical treatment of the compunds of the invention takes place according to the usual standard methods. For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides reference is made to the following standard work: Sucker, Fuchs, Speiser, Pharmazeutische Technologie, Thieme-Verlag Stuttgart, 1978.

The application can be to the skin or mucous membrane or in the interior of the body and can be oral, peroral, enteral, pulmonary, rectal, nasal, vaginal, lingual, intervenous, intraarterial, intracardial, intramuscular, intraperitoneal, intracutanous, suboutanous. The parenteral preparations are especially sterile or sterilized products.

The combination of the invention can also be one product in which the two individual active substances are present in separate formulations so that a separate administration or even an administration which is spaced in time is possible.

If such operation formulations are present, they are adapted to each other and contain the particular active substances in the dosage unit in the same amounts and corresponding weight proportions in which they can be present in the combined mixture.

It is also possible in the case of separate use that both combination partners are not administered at the same time. In such instances, for example, the selegiline can be administered once a day (dose e.g. 5-30 mg) and the amantadine at the same time (dose e.g. 50-200 mg) and then in 3 to 4 other doses (e.g. between 50-200 mg) at 4 hour intervals.

In the liquid preparations the amantadine is present, for example, in concentrations of 2-10, preferably 4-6, especially 5% by weight and the selegiline in concentrations of 0.1-1, preferably 0.3-0.5, especially 0.375% by weight.

For preparations in which the combination of the invention is suspended in molten hard fat and homogenized, 10-50 parts by weight hard fat are used, for example, per 1 part by weight amantadine (in the combination) or per 1 part by weight selegiline (if the selegiline is present as a separate formulation), whereby 0.01-1 part by weight (in relation to 1 part by weight amantadine) soybean lecithin can optionally be mixed in in addition.

For the production of preparations in the form of tablets or capsules, 0.01-0.5 parts by weight starch or gelatine or 0.005-0.3 parts by weight vinyl pyrrolidone-vinyl acetate copolymerizate per 1 parts by weight amantadine (in the combination) or per 1 part by weight selegiline (if the selegiline is present as separate formulation) are used for granulation. 0.01-10, preferably 0.05–1 part by weight calcium hydrogen phosphate per 1 part by weight amantadine (in the combination) or per 1 parts by weight selegiline (if the selegiline is present as separate formulation) can be optionally mixed in . The granulate obtained is dried, e.g. with air whose temperature is between 50°–70° C. The dry granulae can be homogeneously mixed by way of example with 0.0005 to 0.1 part by weight magnesium stearate, 0.001–0.1 part by weight silicon dioxide and/or 0.05–2 parts by weight (the parts by weight indicated previously are per 1 part by weight amantadine (in the combination) or per 1 part by weight selegiline (if the selegiline is present as separate formulation)).

The salts of course should be pharmaceutically acceptable salts. As acids for making the salts, there can be mentioned for example, hydrohalic acids, e.g. hydrochloric acid, hydrobromic acid and hydriodic acid, sulfuric acid, acids of phosphorus, e.g. phosphoric acid and phosphorous acid, nitric acid, perchloric acid, organo mono, di, or tricarboxylic acids of the aliphatic, alicyclic aromatic or heterocyclic series as well as sulfonic acids. Examples of these are alkanoic acids such as formic acid acetic acid, propionic acid, valeric acid, alkanedioc acids, e.g. succinic acid, malonic acid, oxalic acid, and adipic acid, hydrocarboxylic acid, e.g. glycolic acid, lactic acid, malic acid, tartaric acid, citric acid, and ascorbic acid, maleic acid, furmaric acid, hydroxymaleic acid, pyruvic acid, phenylacetic acid, benzoic acid, p-aminobenzoic acid, anthranilic acid, p-hydroxybenzoic acid, salicyclic acid or p-aminosalicylic acid, embonic acid, alkanesulfonic acid, e.g. methanesulfonic acid, ethanesulfonic acid and butanesulfonic acid, hydroxyalkanesulfonic acids, e.g. hydroxyethanesulfonic acid, e.g. 0-chlorobenzenesulfonic acid, p-chlorobenzenesulfonic acid, m-chlorobenzenesulfonic acid, o-bromobenzenesulfonic acid, p-bromobenzenesulfonic acid, toluenesulfonic acid, e.g. p-toluenesulfonci acid, o-toluenesulfonic acid or beta aphthalenesulfonic acid, or sulfanilic acid.

The composition can comprise, consist essentially of or consist of the stated materials and the process can comprise, consist essentially of or consist of the recited steps with such materials.

DETAILED DESCRIPTION OF THE PREFERRED EMBODIMENT

EXAMPLE 1

Injection solution with 10 mg amantadine hydrochloride and 7.6 mg selegiline hydrochloride.

25 g amantadine hydrochloride and 1.875 g selegiline hydrochloride are dissolved successively in 450 ml water gassed with nitrogen for purposes of injection. The solution is filled to 500 ml with water gassed with nitrogen for purposes of injection and after a careful mixing and a further gassing with nitrogen, it is filtered through a membrane filter with a pore width of 0.2 μm with a glass fiber roughing filter until terile. The filtrate is filled under asceptic conditions as well as undern itrogen gassing into colorless ampoules, content 2 ml. 2 ml of the solution contain 100 mg amantadine hydrochloride and 7.5 mg selegiline hydrochloride.

EXAMPLE 2

Capsules with 100 mg amantadine hydrochloride and 7.5 mg selegiline hydrochloride.

10 kg amantadine hydrochloride are intensively mixed with a suitable mixer with 0.75 kg selegiline hydrochloride. Then, the mixture is granulated in a known manner in a fluid bed spray granulation apparatus with a solution of 0.25 kg gelatine in 2.25 kg water. After 0.85 kg corn starch, 0.1 kg magnesium stearate and 0.05 kg highly dispersed silica have been mixed in, the mixture is filled in a filling amount of 120 mg per capsule into hard gelatine capsules of size 2. One capsule contains 100 mg amantadine hydrochloride and 7.5 mg selegiline hydrochloride.

The entire disclosure of German priority application P3612702.7 is hereby incorporated by reference.

What is claimed is:

1. A product containing as active substances, (1) amantadine or a salt thereof with a physiologically acceptable acid and (2) selegiline or a salt thereof with a physiologically acceptable acid, the amount of (1) and (2) being such that the product contains 0.4 to 800 parts by weight amantadine for each one part by weight selegiline and the amounts of (1) and (2) are sufficient to have a synergistic effect in treating Parkinsonism, depression, narcolepsy or cerebro-organic psychosyndrome.

2. A product according to claim 1 containing 20 to 800 mg amantadine and 1 to 50 mg selegiline.

3. A product according to claim 2 containing 50 to 600 mg amantadine and 3 to 40 mg selegiline.

4. A method of treating Parkinsonism, depression, narcolepsy or cerebro-organic psychosyndrome comprising administering to a patient in need thereof the product of claim 1.

5. A method according to claim 4 wherein there is treated Parkinsonism and there is administered the product of claim 1 with the amount of (1) and amount of (2) being sufficient to have a synergistic effect in alleviating the symptoms of Parkinsonism.

* * * * *